United States Patent
Haniff et al.

[11] Patent Number: 6,010,461
[45] Date of Patent: Jan. 4, 2000

[54] MONOLITHIC SILICON INTRA-OCULAR PRESSURE SENSOR AND METHOD THEREFOR

[75] Inventors: Tariq M. Haniff, Campbell; Martin Lim, Redwood City; Yongli Huang, San Jose; Kevin Montegrande, Los Gatos, all of Calif.

[73] Assignee: SiTek, Inc., Campbell, Calif.

[21] Appl. No.: 09/145,150

[22] Filed: Sep. 1, 1998

[51] Int. Cl.$^7$ ........................................... A61B 5/00
[52] U.S. Cl. .............................. 600/561; 603/398; 604/19
[58] Field of Search ......................................... 600/398, 399, 600/401, 405, 561; 604/19, 27, 43; 73/720, 721

[56] References Cited

U.S. PATENT DOCUMENTS

| | | | |
|---|---|---|---|
| 4,166,269 | 8/1979 | Stephens et al. | 338/3 |
| 4,870,964 | 10/1989 | Bailey, Jr. et al. | 128/303.1 |
| 4,874,500 | 10/1989 | Madou et al. | 204/412 |
| 4,993,143 | 2/1991 | Sidner et al. | 29/621.1 |
| 5,062,302 | 11/1991 | Petersen et al. | 73/754 |
| 5,189,777 | 3/1993 | Guckel et al. | 29/424 |
| 5,357,807 | 10/1994 | Guckel et al. | 73/721 |
| 5,631,198 | 5/1997 | Hartauer | 438/53 |
| 5,662,611 | 9/1997 | Beiser et al. | 604/118 |
| 5,668,319 | 9/1997 | Garabedian | 73/514.09 |
| 5,701,905 | 12/1997 | Esch | 128/673 |
| 5,711,302 | 1/1998 | Lampropoulos et al. | 128/672 |
| 5,719,069 | 2/1998 | Sparks | 437/59 |
| 5,810,765 | 9/1998 | Oda | 604/31 |
| 5,879,572 | 3/1999 | Folsom et al. | 216/49 |

*Primary Examiner*—Cary O'Connor
*Assistant Examiner*—Charles Marmor, IV
*Attorney, Agent, or Firm*—Flehr Hohbach Test Albritton & Herbert LLP

[57] ABSTRACT

A silicon monolithic miniature intra-ocular pressure sensing probe utilizes pressure sensing piezoresistors attached to a silicon pressure sensing membrane which is directly exposed to the irrigating fluid used during an eye operation, for example. From a silicon fabrication point of view, this is a micro electromechanical (MEM) device and the integration of the piezoresistive pressure sensor directly into the cannula which is inserted into the eye is partially made possible by providing p++ etch stops to gain access for electrical connection to the piezoresistive elements arranged in a Wheatstone bridge configuration. The silicon sensing membrane forms a smooth surface to avoid turbulence and is close to the eye to minimize error.

3 Claims, 4 Drawing Sheets

MONOLITHIC SILICON INTRA-OCULAR PRESSURE SENSOR AND METHOD THEREFOR

The present invention is directed to a monolithic silicon intra-ocular pressure sensor and a method of construction therefor and, more specifically, to a sensing probe having a cannula end portion for insertion into a human eye for irrigation or for sensing the intra-ocular pressure (IOP) of fluid in the interior of the eye.

BACKGROUND OF THE INVENTION

During eye surgery, techniques to flush the cavities of the eye are hindered by the need to apply a tonometer and then manually adjust the flow to maintain proper pressure. Moreover, devices that continuously monitor intra-ocular pressure (IOP) often deliver erroneous values due to the sensor's distance from the eye. The mounting of a sensor closer to the eye entails mechanical problems due to the micro-miniature (that is several millimeters) size of the sensing probe and the fluid delivery system and the need to minimize surgical trauma.

OBJECT AND SUMMARY OF INVENTION

It is, therefore, an object of the present invention to provide a monolithic silicon intra-ocular pressure sensor and method therefor.

In accordance with the above object, there is provided an intra-ocular pressure (IOP) sensing probe having a cannula end portion for insertion into an eye for irrigation or for sensing the IOP of fluid in the interior of the eye comprising a monolithic silicon sensor/cannula having a cannula portion, a flow channel portion for receiving fluid from an external source, and pressure sensing piezoresistors attached to a silicon pressure sensing membrane which is directly exposed to said fluid.

From a method standpoint, there is provided a micro electromechanical (MEM) process of making an intra-ocular pressure (IOP) sensing probe having a cannula end portion for insertion into the eye for irrigation or for sensing IOP of fluid in the interior of the eye comprising the following steps. In a first semiconductor silicon wafer, fabricating a plurality of flow channels with a cannula end and a fluid input end and having an open top. In a second semiconductor wafer, fabricating a plurality of pressure sensors having wheatstone bridge-type piezoresistive elements adjacent to a pressure deformable silicon membrane in a mirror configuration of the flow channels. Aligning with and monolithically bonding said flow channels to said mating pressure sensors and releasing the bonded components by through wafer etching.

DETAILED DESCRIPTION OF PREFERRED EMBODIMENT

Figure 1:
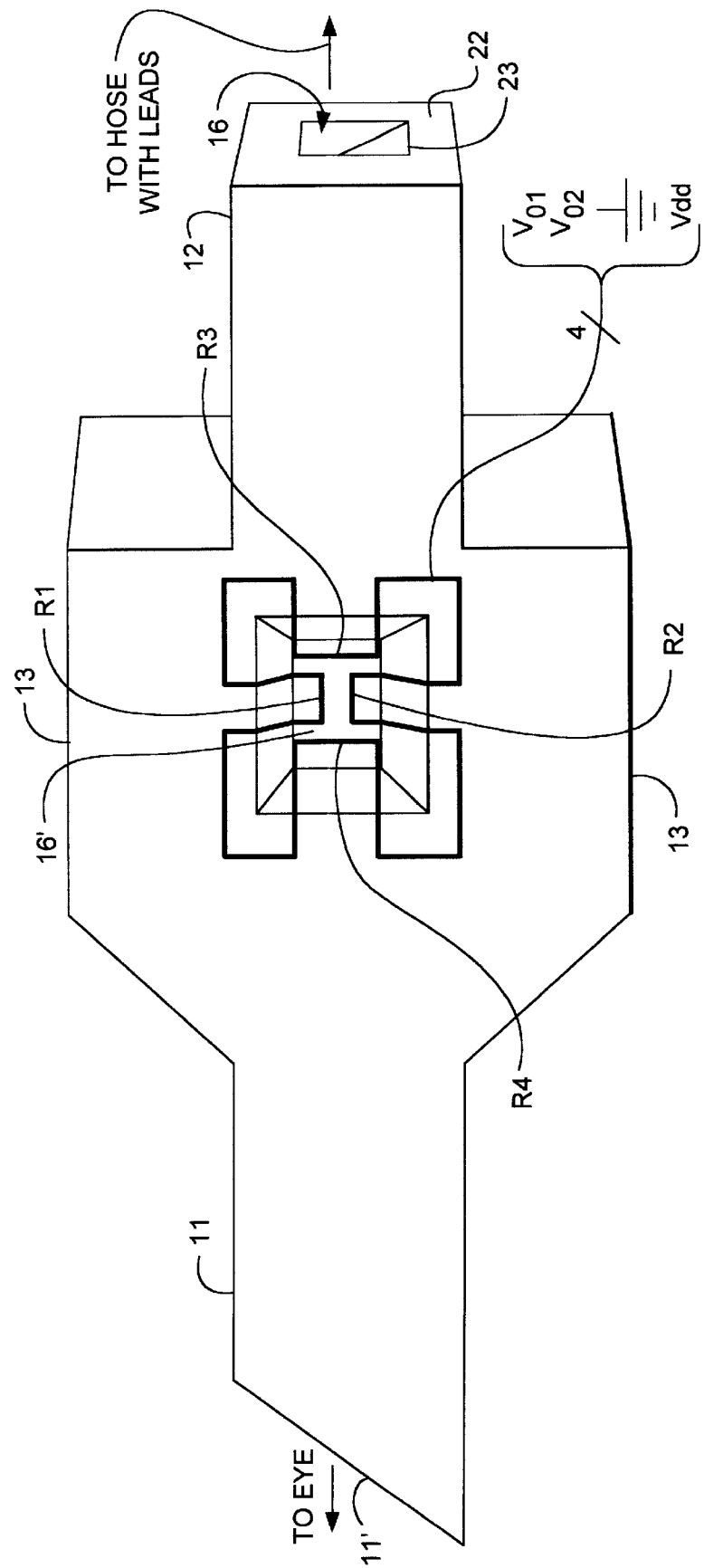
FIG. 1 is a perspective view which is simplified of an intra-ocular pressure sensing probe incorporating the present invention.

FIG. 1 illustrates in a simplified schematic view (especially with regard to the pressure sensing chamber) an intra-ocular pressure sensor probe in which the probe has a cannula end portion 11 which is inserted into the eyeball, typically of a human being, for irrigation and/or fluid pressure sensing purposes and a fluid input end 12 which, as indicated, is connected to a fluid supply hose which would carry various electrical leads. Intermediate the two ends 11 and 12 is an extended pair of shoulders 13 to provide a mechanical stop for the cannula end portion 11. Input end portion 12 receives fluid through the flow channel 16 which has a cross-section of approximately 0.5 millimeter. The entire structure is micro-miniature in size and would be, for example, less than 10 millimeters in length and having a width of approximately 1 millimeter.

As illustrated in a representational manner only, the flow channel 16 for the fluid is shown again at 16' where four pressure sensing piezoresistors are attached (actually embedded) to a silicon pressure sensing membrane (not directly shown) which is directly exposed to the fluid in the flow channel to measure its pressure. The four piezoresistors are representationally illustrated as opposed pairs R1 and R2 and opposed orthogonal pairs R3 and R4. The pressure sensing chamber is actually sealed and is shown open only for illustrative purposes. As will be described in detail below (see FIG. 5), the piezoresistors are connected in a Wheatstone bridge format and as indicated there are four electrical leads 4 including ground, supply voltage, $V_{dd}$, and then a pair of voltages, $V_{O1}$ and $V_{O2}$, the difference of which, $V_{out}$, provides a measure of pressure.

Since the pressure sensor is in very close proximity to the interior of the eye, there is very little pressure drop in, for example, the 4 to 5 millimeter flow channel distance to the interior of the eye. Therefore, a very precise pressure measurement is made. In normal practice, the fluid supply system would utilize the voltage output of the pressure sensing probe to provide for automatic feedback control to maintain the pressure of the fluid in the eye to an exact desired amount.

Finally, as illustrated in FIG. 1, the cannula end portion 11 has a beveled tip 11' for easy insertion into the incision of the eye. Also, the shoulders 13 and their transition to cannula 11 may either be right-angled or beveled as shown. As will be discussed below, very sharp angles are possible because of the deep plasma etching technique used in the fabrication of the device of FIG. 1.

Figure 2B:
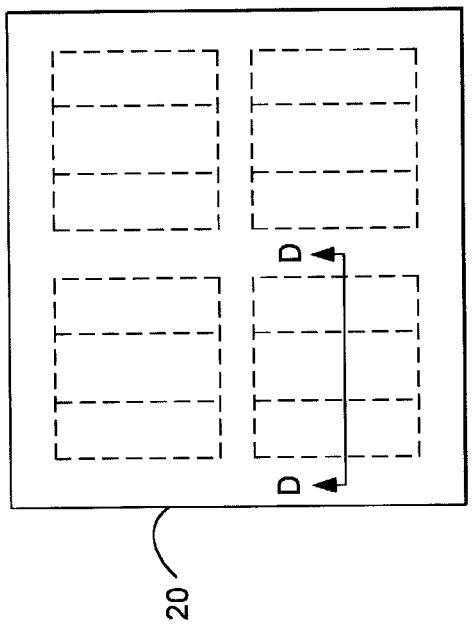
FIGS. 2A–2G are plan and cross-sectional views showing the construction of the device of the present invention.
Figure 2D:
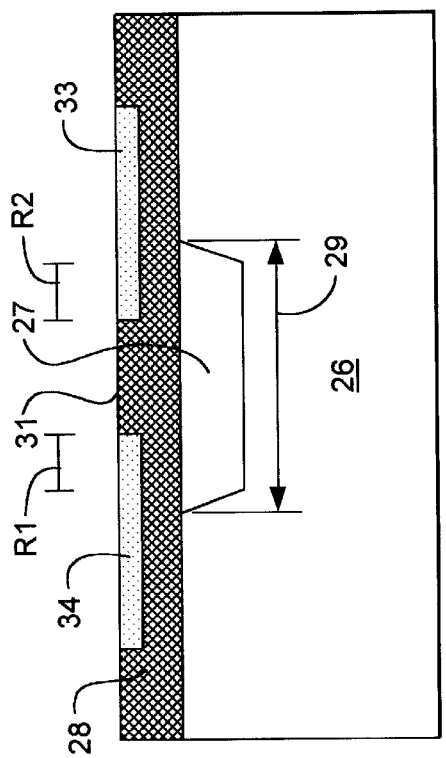
Figure 2A:
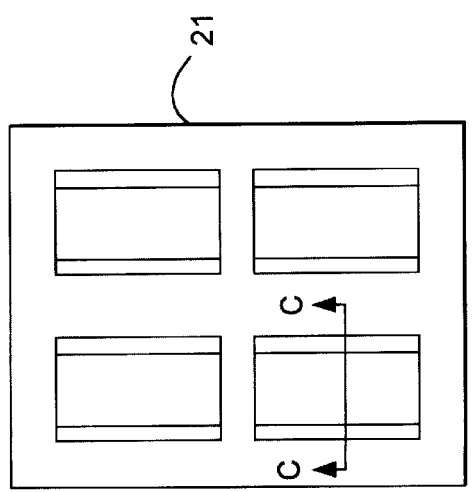
Figure 2C:
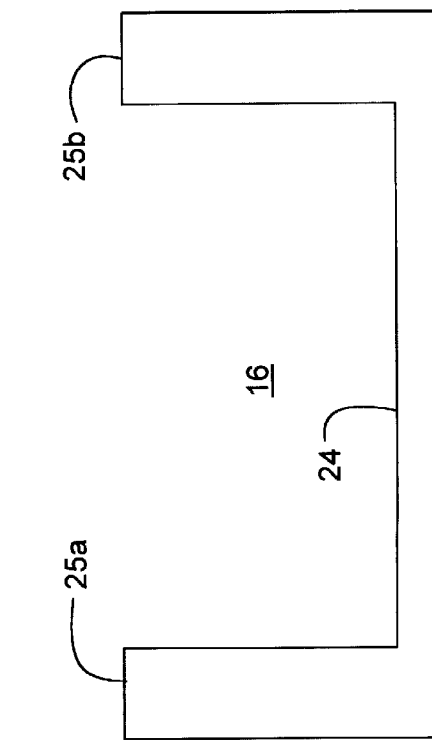

Such fabrication is illustrated in FIGS. 2A–2G. Initially as illustrated in FIGS. 2A and 2B, two separate silicon wafers 20 and 21 are used where in wafer 21 a plurality of flow channels are fabricated (depending on the size of the wafer several hundred although only four are indicated for purposes of illustration) and as shown by the cross-section 22 illustrated in FIG. 2C, across the section C—C indicated in FIG. 2A. The flow channel has a cannula end 11, a fluid input end 12 and an open top. The cross-section indicated as 22 is in effect shown in FIG. 1 where it is terminated by the dashed line 23. Specifically, the flow channel is U-shaped with a bottom 24 and with legs 25a, 25b to thus provide an open top.

FIG. 2B illustrates the other semiconductor wafer 20 where a plurality of pressure sensors are fabricated. A cross-section is illustrated in FIG. 2D across the section D—D indicated in FIG. 2B. Except as will be indicated below, this is a standard pressure sensor having a silicon base 26, a U-shaped cavity 27 with an n-type silicon layer 28 covering the cavity. The portion 29 of layer 28 overlying the cavity is in effect a silicon pressure sensing membrane. When the top 31 of this membrane 29 is exposed to the fluid in the channel 16, it will deform and the amount of deformation as indicated by the piezoelectric resistors. Two of them are partially shown as R1 and R2. They are, of course, an integral part of membrane 29 and layer 28. Then, in accordance with the invention a p++ layer is diffused in the "n" layer 28 in electrical contact with the piezoresistive elements R1 and R2. These layers indicated in a darker format are 33 and 34.

Figure 2E:
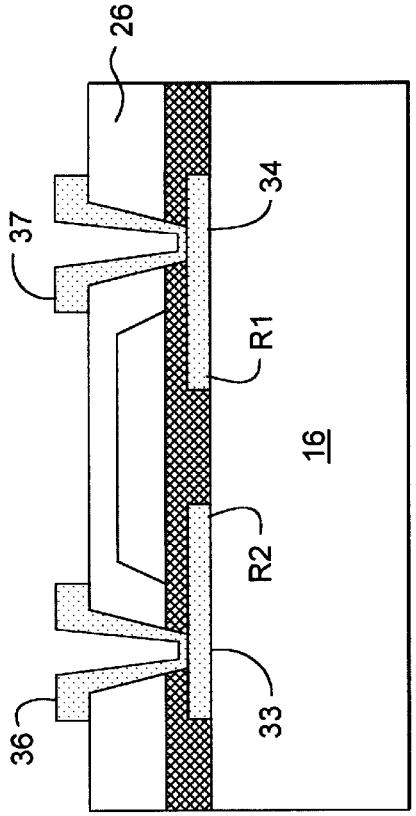
Figure 2F:
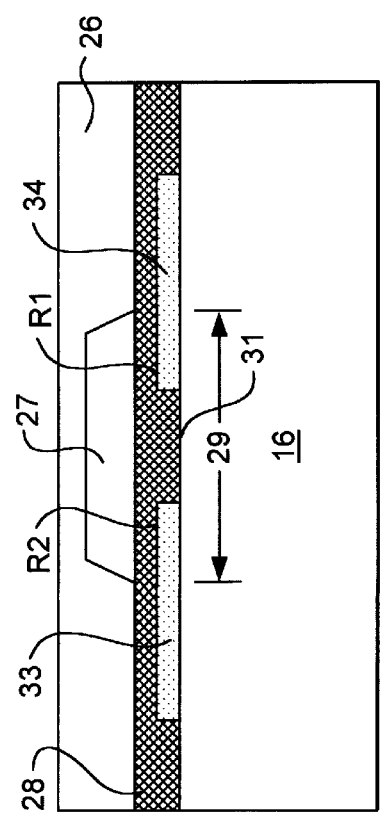

In the next step as illustrated in FIG. 2E, the wafer 21 of FIG. 2A is flipped and bonded to the wafer 20 of FIG. 2B. Thus, the surface 31 of the silicon membrane 28 is exposed to the fluid in the enclosed flow channel 16 which has been formed by the above process. The silicon base 26 is then thinned to the size shown. FIG. 2F illustrates the opening of vias or contact openings which is accomplished with potassium hydroxide (KOH). This etching in accordance with the present invention is stopped by the p++ areas 33 and 34. When the n-silicon areas 28 are heavily doped near their solid solubility limit by a p-type material, they display a great resistance to etching in KOH. Thus, they serve as natural etch stops for the via formations.

Figure 5:
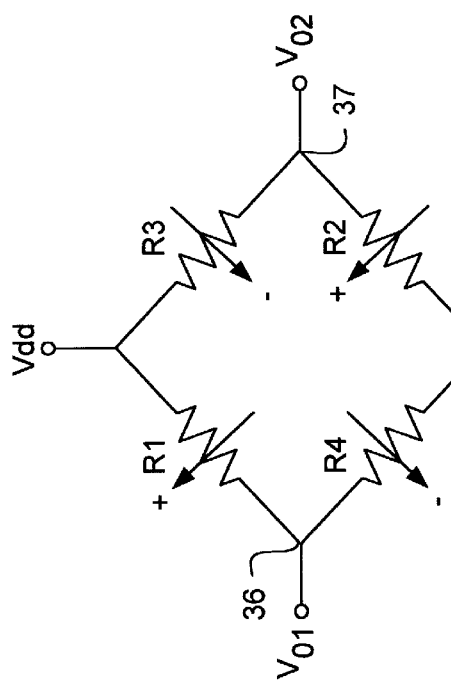
FIG. 5 is a schematic circuit representation of FIG. 4.

After the etch procedure, aluminum metallizing 36 and 37 provides contacts. Referring to FIG. 5, these contacts would occur at the points indicated on the Wheatstone bridge circuit shown. The other two resistors, R3 and R4, are located in an orthogonal location and thus the crystallin structure of the membrane 29 is different. Thus, the arrows shown in FIG. 5 indicate when the membrane is moved by ambient fluid pressure a positive resistance change occurs for R1 and R2 and a relative negative change for R3 and R4. This relative change is known in the art.

Figure 2G:
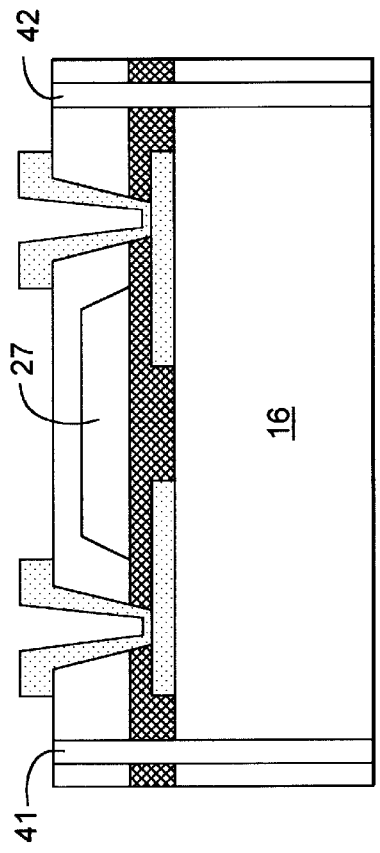
Figure 3:
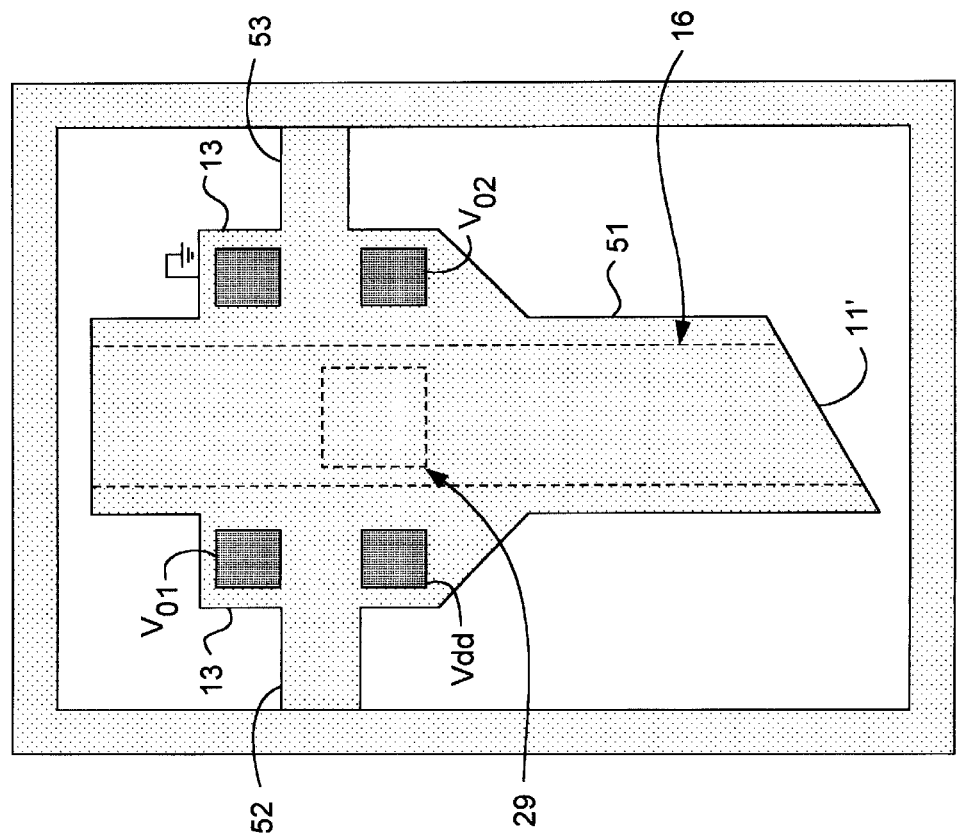
FIG. 3 is a plan view illustrating a step in the construction of the present invention.

As shown in FIG. 2G, by using a high density ionized gas through wafer etching is accomplished as indicated at 41 and 42 to release the individual bonded components. FIG. 3 shows the process in greater detail where the actual mask pattern is shown at 51. The silicon pressure sensing membrane outline is illustrated at 29. And the four electrical contacts discussed in FIG. 1 are shown by the dark portions and are appropriately labeled. The deep through wafer etching, however, does not release the bonded components of each pressure sensing probe completely but rather a pair of tethers 52 and 53 still retain the sensing probe. Then at the appropriate time, the tethers are broken to remove the bonded silicon components or pairs for final connection to a hose with leads (FIG. 1).

Figure 4:
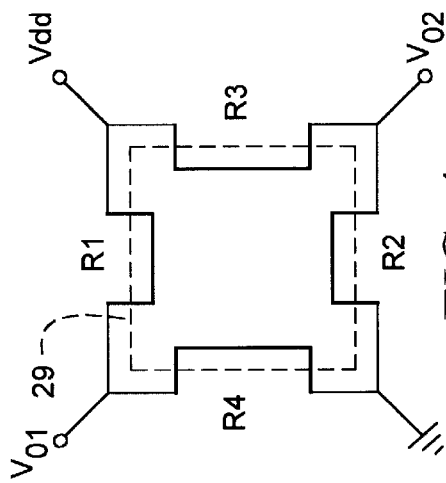
FIG. 4 is a simplified cross-sectional view of a portion of FIG. 3 illustrating piezoresistive elements.

FIG. 4 illustrates the pressure sensing membrane 29 and its relationship to the four piezoresistive elements R1, R2, R3 and R4. Also, the electrical contacts relative to FIG. 3 are labeled.

Referring to FIGS. 2E, 2F and 2G, it is apparent that the pressure sensing membrane 29 forms a continuous planar portion of the flow channel 16 so that no fluid turbulence is caused. Then, as discussed above, since the entire structure is made of a monolithic semiconductive material, such as silicon, it is possible to fully integrate the pressure sensor with the flow channel and cannula to locate the pressure sensor very close to the end of the cannula which is inserted into the eye to minimize error causing pressure drop in the flow channel. Also, no turbulence is introduced. This is all made possible by the monolithic construction described above. Thus, both an improved intra-ocular pressure sensor miniature structure has been provided along with a novel fabrication method which includes, of course, the use of the p++ etch stop. This, again, provides easy electrical access to the piezoresistive elements.

What is claimed is:

1. An intra-ocular pressure (IOP) sensing probe having a cannula end portion for insertion into an eye for irrigation or for sensing the IOP of fluid in the interior of the eye comprising:

a monolithic silicon sensor/cannula having a cannula end portion, a flow channel portion for receiving fluid from an external source, and pressure sensing piezoresistors attached to a silicon pressure sensing membrane which is directly exposed to said fluid from said external source.

2. An intra-ocular pressure sensing probe as in claim 1 where said monolithic silicon sensor/cannula includes intermediate extending shoulder means for providing a mechanical stop for said cannula end portion.

3. An IOP sensing probe as in claim 1 where said sensing membrane forms a continuous planar portion of said flow channel whereby no fluid turbulence is caused.

* * * * *